(12) United States Patent
Baldwin et al.

(10) Patent No.: US 9,357,933 B2
(45) Date of Patent: Jun. 7, 2016

(54) CONTINUOUS, NON-INVASIVE, OPTICAL BLOOD PRESSURE MONITORING SYSTEM

(76) Inventors: Donna Baldwin, Murrieta, CA (US); Matthew James Baldwin, Murrieta, CA (US)

( * ) Notice: Subject to any disclaimer, the term of this patent is extended or adjusted under 35 U.S.C. 154(b) by 61 days.

(21) Appl. No.: 13/008,671

(22) Filed: Jan. 18, 2011

(65) Prior Publication Data
US 2011/0178415 A1    Jul. 21, 2011

Related U.S. Application Data

(60) Provisional application No. 61/336,159, filed on Jan. 19, 2010.

(51) Int. Cl.
*A61B 5/021* (2006.01)
*A61B 5/00* (2006.01)
*A61B 5/024* (2006.01)

(52) U.S. Cl.
CPC ............... *A61B 5/021* (2013.01); *A61B 5/0059* (2013.01); *A61B 5/024* (2013.01)

(58) Field of Classification Search
CPC .... A61B 5/0261; A61B 5/021; A61B 5/1455; G03H 1/0005
USPC .................. 600/310, 480, 485; 356/457, 458
See application file for complete search history.

(56) References Cited

U.S. PATENT DOCUMENTS

| | | | |
|---|---|---|---|
| 3,215,135 A | | 11/1965 | Franke |
| 3,249,105 A | | 5/1966 | Polanyi |
| 4,643,514 A | * | 2/1987 | Raviv et al. .............. 600/108 |
| 4,725,142 A | * | 2/1988 | Sharnoff ................... 356/458 |
| 5,014,709 A | * | 5/1991 | Bjelkhagen et al. ....... 600/431 |
| 5,158,091 A | | 10/1992 | Butterfield et al. |
| 5,341,805 A | * | 8/1994 | Stavridi et al. ............ 600/316 |
| 5,987,995 A | | 11/1999 | Sawatari et al. |
| 6,006,119 A | * | 12/1999 | Soller et al. ............... 600/322 |

(Continued)

OTHER PUBLICATIONS

Wang, et al., "A linear relation between the compressibility and density of blood", J. Acoust. Soc. Am. 2001 109 (1) 390-6.

(Continued)

*Primary Examiner* — Patricia Mallari
*Assistant Examiner* — Michael Catina
(74) *Attorney, Agent, or Firm* — Knobbe Martens Olson & Bear LLP

(57) ABSTRACT

Various embodiments of the invention disclosed herein comprise a system of wearable devices that collectively allow for the continuous, non-invasive, measurement and monitoring of blood pressure, without the use of an inflatable cuff. The system incorporates: 1) An optical module, which is comprised of a coherent source of light, a semi-transparent hologram, optics for viewing the interference pattern developed between the illuminated hologram and arterial blood, a Charge-Coupled Device (CCD) array, and processing electronics with Bluetooth capability that facilitates digitization and wireless transmission of the fringe pattern to, 2) a personal digital assistant (PDA) that is worn on a waist belt. The PDA and associated software allow for continuous calculation and monitoring of real-time arterial blood pressure from the digitized fringe patterns received. The system further comprises 3) a personal computer (PC) with wireless capacity and connection to the internet. Continuous BP function, alerts, condition and medical assessment is conducted through PDA-PC communications with internet based medical facility.

16 Claims, 4 Drawing Sheets

(56) References Cited

U.S. PATENT DOCUMENTS

| | | |
|---|---|---|
| 6,263,227 B1 * | 7/2001 | Boggett et al. ............... 600/407 |
| 6,533,729 B1 * | 3/2003 | Khair et al. ................. 600/503 |
| 7,179,228 B2 | 2/2007 | Banet |
| 2008/0188726 A1 * | 8/2008 | Presura et al. ............... 600/322 |
| 2009/0163796 A1 * | 6/2009 | Simpson et al. ............. 600/407 |
| 2009/0275812 A1 * | 11/2009 | Reichgott et al. ............ 600/310 |

OTHER PUBLICATIONS

Kreis, "Handbook of Holographic Interferometry: Optical & Digital Methods", Chapter 7, 2005, Wiley-VCH GmbH & Co. KGaA, Weinheim.

\* cited by examiner

CONTINUOUS, NON-INVASIVE, OPTICAL BLOOD PRESSURE MONITORING SYSTEM

CROSS-REFERENCE TO RELATED APPLICATIONS

This application claims the priority of U.S. Provisional Application No. 61/336,159 entitled "Continuous, Non-Invasive, Optical Blood Pressure Monitoring System" filed on Jan. 19, 2010, the entire contents and substance of which are hereby incorporated in total by reference.

FIELD OF INVENTION

The present invention relates to blood pressure monitoring systems. More specifically, the present invention relates to a non-invasive, wearable, cuff-less blood pressure system having optical and wireless components.

BACKGROUND OF THE INVENTION

Cardiac contraction during a heartbeat causes a time dependent flow of blood in the arteries of the body. The flow of blood in a single beat is pulse-like and caused by a rise in the pressure of the blood from a static value, called the diastolic pressure, to a maximum value at the peak of the pulse, called the systolic pressure. The pulse-like variation in blood pressure induces a corresponding pulse-like variation in the refractive index of the blood plasma. That is, the variation of blood pressure in a heart beat induces a variation in the optical properties of the blood.

Conventional blood pressure monitoring devices typically involve measuring blood pressure with an inflatable cuff, whether automated, or by manual inflation. In these arrangements, the cuff is placed around a patient's arm, directly over an artery. The cuff inflates in order to compress the underlying artery of the patient, and cut off the circulation to the arm. The cuff then deflates slowly and releases pressure on the arm and allows for the determination of systolic and diastolic readings by direct observation or measurement of Korotkoff sounds. The most common manual and automated blood pressure monitors involve inflating and deflating a cuff and is both time consuming and involves some discomfort for the patient.

Continuous measurement of blood pressure by means of optically based pressure transducer tips, inserted into the blood stream using a catheter, have been proposed, as illustrated in U.S. Pat. No. 3,249,105 to Polyanyi, and Franke U.S. Pat. No. 3,215,135, and more recently, to Sawatari et al, U.S. Pat. No. 5,987,995. While these techniques provide a means of measuring blood pressure continuously, and are useful in operative settings, they are invasive, expensive, require medical staff to administer, and are not designed for continuous every day operations.

Non-invasive blood pressure measurement systems include a tissue contact stress sensing system involving measurement of tonometric blood pressure non-invasively using a one-dimensional optical sensor array, as described by U.S. Pat. No. 5,158,091 to Butterfield et al. This method measures a pressure waveform on the skin tissue, which is not the same as the pressure on the artery walls, and therefore necessitates calibration. Calibration is extremely difficult for this type of sensor, and therefore is not expected to provide accurate or reproducible readings.

Recent inventions have introduced non invasive measurement of systolic and diastolic pressure through optical pulse train, and signal processing means. These inventions involve continuous measurement of blood pressure as disclosed in the prior art by U.S. Pat. No. 7,179,228 to Banet. While this technique provides a means of measuring blood pressure in a cuff-less, non invasive setting, it requires prior calibration by the patient, and does not provide the same level of accuracy as other methods.

The abovementioned prior art lacks the advantages of a continuous blood pressure monitoring system that is capable of being worn for continual periods, whilst offering the patient complete mobility. Thus, it is the object of various embodiments of this invention, to provide a means of measuring blood pressure on a continuous or non-continuous basis, using a wearable, cuff-less, non-invasive method, for every day use. It is a further object of various embodiments of the invention to provide a mobile system that transmits patient vitals on a continuous basis using a wireless sensor network. The advantage of such a system is that it can be used in any setting requiring continuous vital signs measurement in a mobile environment whether it be monitoring of soldier's vital signs on the battlefield, in a homecare environment on a daily basis where mobility is critical, or even by astronauts on board a space craft or station.

SUMMARY OF THE INVENTION

Various embodiments of the present invention comprise a system of wearable devices that collectively allow for the continuous, non-invasive, measurement and monitoring of blood pressure, without the use of an inflatable cuff, using digital holographic interferometer measurements. Optical fringe patterns are compared using a holographic interferometric technique, to determine the systolic and diastolic pressures by comparing time averaged refractive index changes within the blood.

A processing module, comprised by the wearable system and configured to receive a set of time dependent interferometric optical information in a digital format, compares it to a mathematical theory to calculate blood pressure parameters, and determines systolic and diastolic blood pressure readings continuously by means of a holographic interferometric arrangement. The consecutive time multiplexed images determine systolic and diastolic points through refractive index changes imaged by the optical assembly and Charge-Coupled Device (CCD) array. Further processing electronics and software within the Personal Digital Assistant (PDA), correlate the refractive index changes over time, to systolic and diastolic readings. This data is sent wirelessly from the optical module, to the PDA, and to the server via Wide Area Network (WAN).

BRIEF DESCRIPTION OF THE DRAWINGS

These and further features and advantages of various embodiments of the invention will be described in the following detailed description herein with reference to the following drawings wherein.

DETAILED DESCRIPTION OF THE INVENTION

Figure 1:
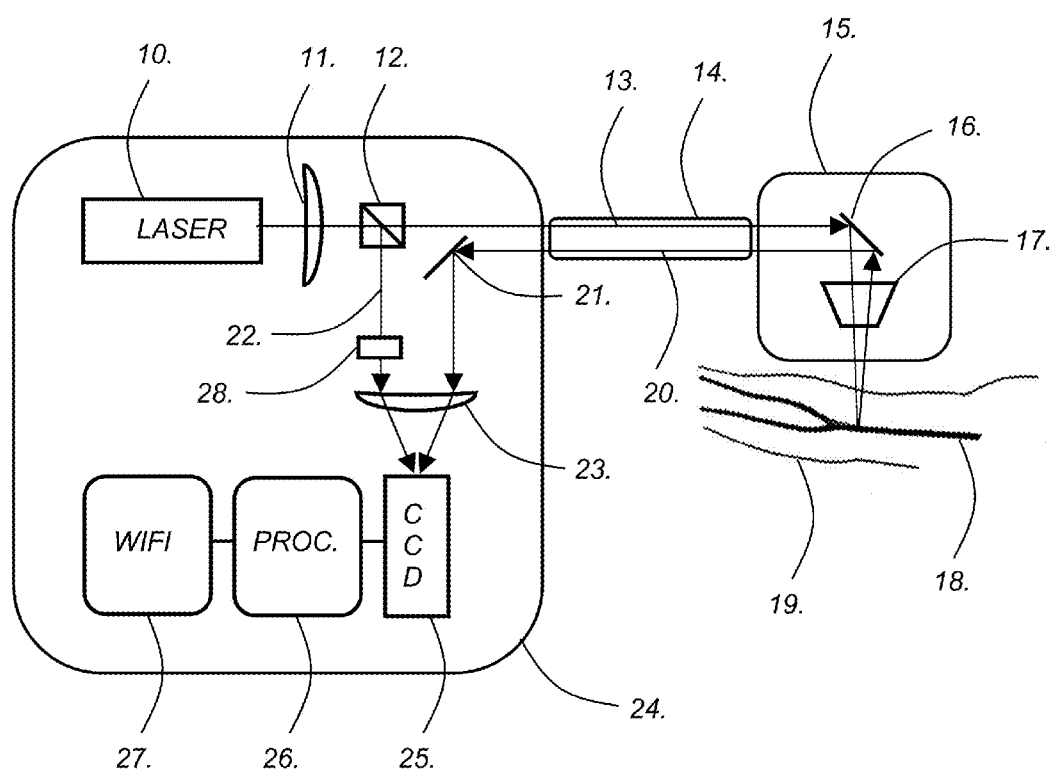
FIG. 1 describes the optical module which encompasses the holographic interferometer, laser assembly, CCD array, and a sectional view of the optical patch with connecting optical fibers to the optical module described in FIG. 1.

In accordance with various embodiments of the present invention, and with reference to FIG. 1, holographic interferometry is used to measure the time dependent variation of a patient's blood pressure. Blood pressure variation is recorded in the form of successive holographic infererometric fringe patterns during the beat cycle of the heart.

In prior art, a typical arrangement for recording a hologram involves a source of collimated light from a laser that is split into two coherent beams with a beam splitter. One of the beams, termed the object beam, illuminates an object and the light is refocused onto a photographic plate. The second beam, termed the reference beam, is focused directly onto the photographic plate. The light from both beams combines at the plate to form an interference pattern called a hologram. A hologram stores the complete amplitude and phase information of the illuminated object in such a way that re-illumination of the hologram, by the reference beam alone, produces a complete three dimensional virtual image of the original state of the object. Holographic interferometry is an extension of this basic method. If the object is replaced in its original position and re-illuminated with the object beam, optical interference between the illuminated object and the virtual image occurs if the state of the original object is varied in space, geometry or refractive properties and the interference information that results is the basis for holographic interferometry. Holographic interferometry is used to measure transient phenomena and is now a well accepted method for nondestructive testing, vibration analysis, flow visualization and the study of thermal and stress fields, to name a few. In holographic interferometry, any object, or a partially transparent object with varying refractive properties called a 'phase' object, can be interferometrically studied in space and time by comparing a state of the object with the holographic recording of a previous state of the same object. In a more modern form of the technique, digital holographic interferometry uses an electronic imaging system such as a TV camera, or CCD array. This technique allows the consecutively imaged interference patterns to be resolved in real-time.

Referring now to FIG. 1, various embodiments of the invention incorporate a first optical module 24 that forms the basis of a digital holographic interferometer with data storage and wireless communication capability, a second optical module 15 that is a small optical device that is adhered to a patient's skin 19 and is fixed over a sub-dermal artery 18, and an optical fiber bundle connection 14 that connects the first 24 and second 15 optical modules. Devices 24, 15 and 14 when used together, allow holographic interferometry of the sub-dermal artery to be performed and measured.

The first optical module 24 is comprised of a coherent source of light 10 that produces illumination for the purpose of generating a holographic interference pattern of a patient's arterial blood. The illuminating beam is passed through a typical holographic interferometric arrangement consisting of a lens 11 and a beam splitter 12 that separates the beam into an object beam 13 and a reference beam 22. The object beam is coupled into the optical fiber bundle 14 connected to the second optical module 15 while the reference beam passes through a transmission phase hologram 28 (known herein as the Reference Calibration Hologram) and is further focused using a lens 23 onto a CCD array 25. The object beam 13 is re-directed using a reflective surface 16 and focused with a compound optical arrangement 17 onto a sub-dermal region of a patient where an artery to be probed is located. The compound optical arrangement 17 further views the illuminated artery 18 and provides a means for light viewed to be transmitted back as a return object beam 20 to the first optical module via the optical fiber bundle connection 14. The return beam 20 is redirected with a reflective surface 21 and focused onto the CCD array 25 where said return beam illumination produces an interference pattern with the reference beam 22. The interference pattern is digitally recorded and processed with a microelectronic processor 26, and the information, in digital form, is wirelessly transmitted with a conventional wireless communications chipset 27.

Figure 2A:
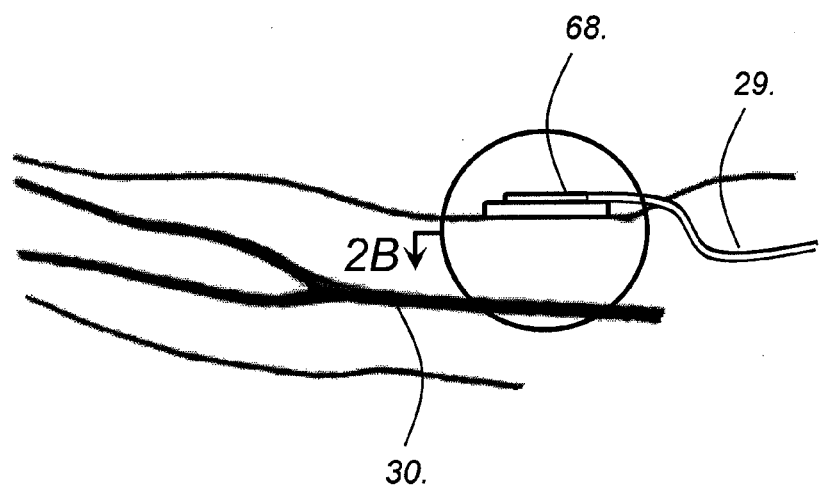
FIG. 2A is a side view of the optical patch, and associated optical fiber connectors as illustrated in FIG. 1A.
Figure 2B:
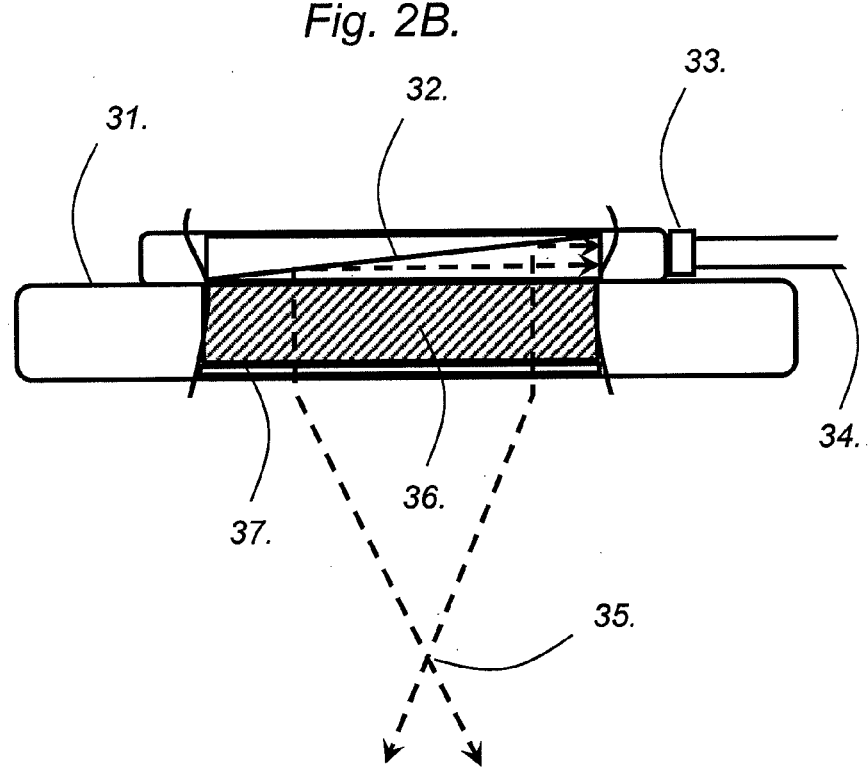
FIG. 2B is a side sectional view of the optical patch illustrating the interference of the beams within the artery's blood volume for determining blood pressure, and associated beam steering optics and fiber optic connections within the optical patch.

FIG. 2A shows an embodiment of the second optical module 68 as worn on a patients arm. In this embodiment the module is positioned with either a band or adhesive means over a region of the arm in such a way that a sub-dermal artery 30 can be illuminated by light transmitted through the optical fiber bundle connection 29. The second optical module further comprises the elements shown in the sectional view of FIG. 2B. The optical fiber bundle 34 is connected to the second optical module 31 by means of a mechanical connection 33. Coherent illumination passes from the optical fiber bundle 34 and connection 33 and is redirected toward the patient's skin with a reflective surface 32. A light diffuser 37 and compound microscope optics 36 focus the light 35 on to the sub-dermal artery. Reflected light is imaged by the same optical arrangement 36, 32 and coupled back into the fiber bundle connection 34.

The flow of blood in a heart beat is pulse-like and caused by a rise in the pressure of the blood from a static value, called the diastolic pressure, to a maximum value at the peak of the pulse, called the systolic pressure. The pulse-like variation in blood pressure induces a corresponding compression of the blood. For an incremental change in blood pressure $\Delta P$, there is a proportional incremental change in the density of the blood $\Delta \rho$, where with the proportionality constant is defined as the compressibility of the fluid $\chi$ (S H Wang et al., J. Acoust. Soc. Am. 2001 109(1) 390-6). Mathematically, $$\chi = \frac{1}{\rho} \frac{\Delta \rho}{\Delta P}. \tag{1}$$

For liquids, the relationship between density and refractive index can be taken from the equation for refractivity $r = n - 1$, substantiated theoretically by the Lorentz-Lorenz equation, $$r = \left((n^2 - 1) - \frac{1}{n^2 + 2}\right)\rho. \tag{2}$$

In various embodiments of the present invention, the change in refractive index of arterial blood with pressure, as described by equations (1) and (2), allow it to be treated as time varying phase object in a holographic interferometric arrangement. Various embodiments of the present invention employ both real-time, and double-exposure holographic interferometric methods. Fringe shift images, produced at the CCD by the change in arterial blood pressure over a heartbeat cycle, are recorded in real time. The fringe shift images result from the double exposure method whereby interference is caused by superposition of the image produced by the semi transparent reference hologram and the light field produced by the arterial blood. The interference phase distribution φ(x, y) in the plane perpendicular to the direction of the light wave, z is given by $$\varphi(x, y) = \frac{2\pi}{\lambda} \int \Delta n(x, y, z) dz.$$

Here λ is the wavelength of incident light, and $\Delta n(x, y, z) = n'(x, y, z) - n_r(x, y, z)$ is the difference between the refractive index of the arterial blood n'(x, y, z) at a time instant of t' in the beat, and the refractive index $n_r(x, y, z)$ of the phase object imaged in the reference hologram. The resulting intensity distribution in the holographic interferogram at the CCD plate is then given by (T Kreis, Handbook of Holographic Interferometry: Optical & Digital Methods 2005 WILEY-VCH GmbH & Co. KGaA, Weinheim)

$$I(x,y) = 2I'(x,y)(1 + \cos(\Delta n(x,y))).$$

The phase object $n_r(x, y, z)$ holographically imaged in the semi-transparent Reference Calibration Hologram, is produced separately by imaging a fluid of similar refractive index to that of human blood in a similar optical geometry to the present invention. The Reference Calibration Hologram is taken at known values of fluid pressure and thereby constitutes a means for calibration of the recorded holographic interferogram of an actual patient by mathematically characterizing the recorded fringe patterns during the heart beat cycle using equations (1)-(4). Holograms are easily reproduced from a master hologram so that the Reference Calibration Hologram is easily mass produced. In another embodiment of the system of wearable devices, the Reference Calibration Hologram could be obtained directly from the patient, but this would require cross calibration with an accepted form of blood pressure measurement such as an inflatable cuff and sphygmometer and is not the preferred embodiment.

Figure 3:
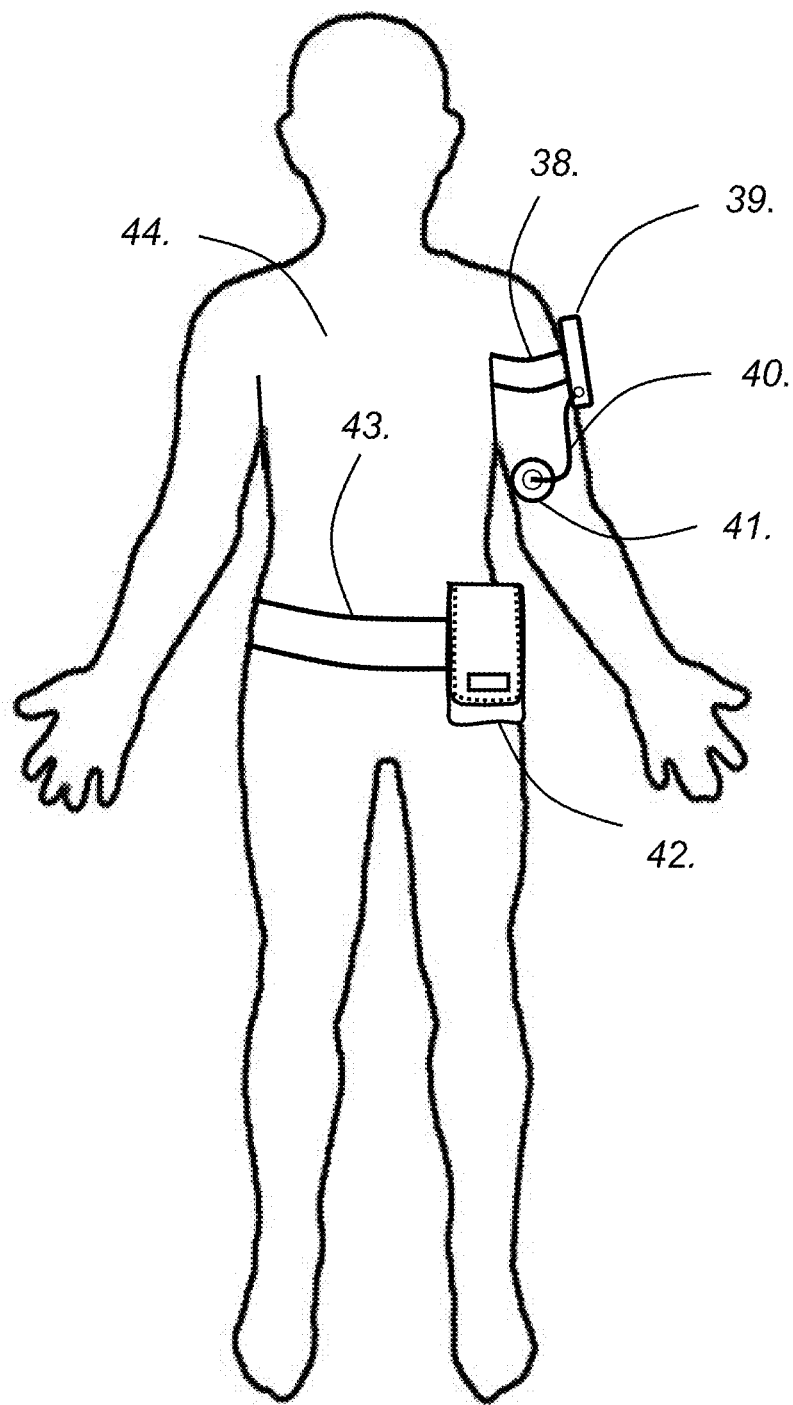
FIG. 3 illustrates the wearable, and mobile aspects of various embodiments of the invention, with the optical module and patch worn on the arm, and the wireless PDA module worn on a belt.

In FIG. 3 the system of wearable devices is shown as worn by a patient 44. In one embodiment, the first optical module 39 is secured to the upper arm of a patient with a belt 38. The second optical module 41 is attached to a location with a sub-dermal artery, not limited to the brachial artery for example, and is connected optically to the first optical module with the optical fiber bundle connection 40. The first and second optical modules are of dimension small enough so as not to be restrictive to normal human activity. Time varying holographic interferometric information is communicated wirelessly by the first optical module using a wireless transmission standard, not limited to Bluetooth™, to a PDA 42, that is worn at the patient's waist on a belt 43, or other convenient location. Analysis software installed on the PDA calculates and monitors the patient's blood vital signs not limited to pulse rate, and diastolic and systolic blood pressure. Long range wireless communication features of the PDA allow for medical monitoring of the patient in a mobile capacity within range of a wireless access point.

Figure 4:
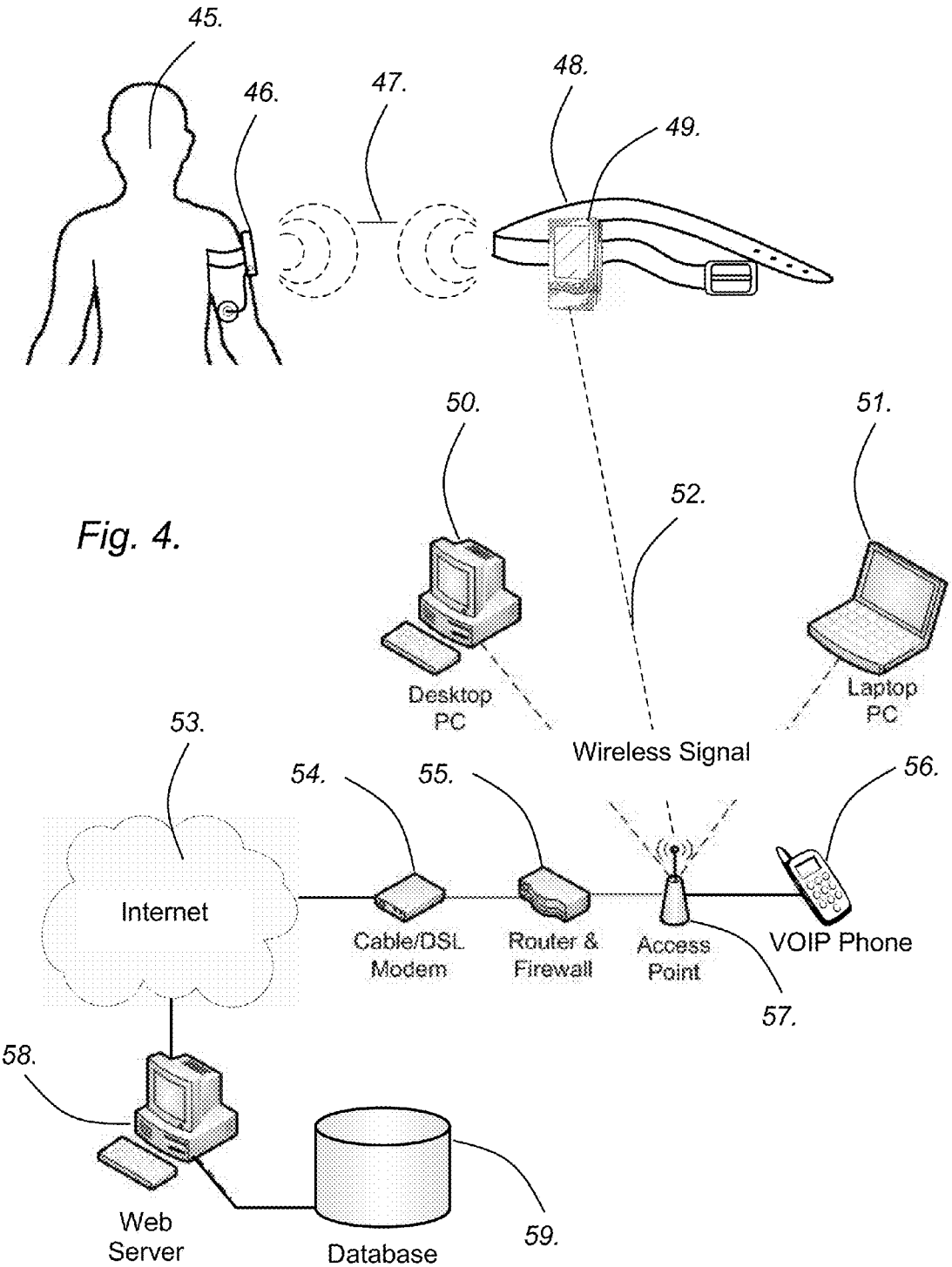
FIG. 4 is a functional system diagram describing the wireless network and wireless transmission of the signal to the WAN and remote server(s).

FIG. 4 shows one embodiment of the present invention integrated with a wireless transmission network and internet based web service for continuous medical monitoring. As depicted, a patient 45 is shown wearing the present invention 46. Holographic interferometric information, in digitized form, and communicated with short range wireless 47, is intercepted with the belt 48 worn PDA 49, and analyzed to yield information on the patient's blood vital signs. The PDA is programmed to continuously monitor and log the patient's vital signs, and also generate emergency alerts that can be triggered automatically or manually by the patient. Both blood vital sign data, and alert status, can be communicated to a wireless transmission network through a local access point 57 using a long range broadband wireless signal 52 generated by the PDA. This information can be stored on the patients desktop PC 50 or laptop PC 51 for the purpose of home monitoring, or communicated to a medical web based internet server 58, offering web services and database storage 59 through the internet 53. Typical internet components such as cable, DSL, or modem connections 54, router 55, or VOIP telecommunication connection 56, may be present in other embodiments.

While the preferred embodiments described herein are intended to illustrate the principles of the invention, it may become apparent by those skilled in the art, that many changes, modifications, variations, and other applications and uses may be evident. Thus, all embodiments, changes, variations modifications, and other uses and applications which do not depart from the scope and spirit of the invention are deemed to be covered by the invention as claimed.

The invention claimed is:

1. A device for the non-invasive measurement of a person's blood pressure parameters comprising:
a first optical module comprising an optical source of coherent light configured to provide light to a second optical module, said first optical module included in a wearable system configured to be worn on the person;
the second optical module included in the wearable system, the second optical module comprising optics configured to be worn proximal to the person's skin, to deliver said coherent light to a sub-dermal region of the person, and to receive light reflected from said sub-dermal region;
an optical connection configured to couple light between the first optical module and the second optical module;
a hologram recorded in a non-transitory medium, said hologram not obtained directly from said person, said hologram configured to provide time dependent interferometric optical information from optical interference using said coherent light reflected from said sub-dermal region;
an electronic imaging system configured to transform the time dependent interferometric optical information into a digital format; and
a processing module configured to receive the time dependent interferometric optical information in a digital format and to calculate blood pressure parameters therefrom.

2. The device of claim 1, wherein said hologram comprises a reference calibration hologram.

3. The device of claim 2, wherein said reference calibration hologram is obtained from a master hologram.

4. The device of claim 2, wherein said reference calibration hologram comprises a holographic image of a fluid that is not blood.

5. The device of claim 1, further comprising a reference arm configured such that said light reflected from said sub-dermal region interferes with light in said reference arm to form interference fringes that are imaged by said electronic imaging system.

6. The device of claim 5, wherein said hologram is disposed in said reference arm.

7. The device of claim 5, further comprising a beamsplitter disposed in an optical path between said optical source of coherent light and said sub-dermal region, said beamsplitter configured to separate light from said optical source into an object beam and a reference beam, said object beam being delivered to said sub-dermal region and said reference beam to said reference arm.

8. The device of claim 7, wherein said hologram is in said reference arm.

9. The device of claim 1, wherein said processing module is included in said wearable system.

10. The device of claim 1, further comprising electronics configured for wireless transmission.

11. The device of claim 10, wherein said electronics configured for wireless transmission is configured to communicate wirelessly with another component worn by said patient.

12. The device of claim 10, wherein said electronics configured for wireless transmission is configured to communicate via long range wireless communication with a component that is not worn by said patient.

13. The device of claim 12, further comprising a component that is not worn by said patient, wherein said component comprises a computing device with wireless capacity and connection to a network.

14. The device of claim 1, wherein said optical source of coherent light comprises a laser.

15. The device of claim 1, wherein said optical connection comprises an optical fiber bundle.

16. The device of claim 1, wherein said non-transitory medium comprises a plate.

* * * * *